United States Patent
Israelsson et al.

(10) Patent No.: US 6,848,574 B1
(45) Date of Patent: Feb. 1, 2005

(54) STORAGE PACKAGE AND A METHOD FOR PACKAGING

(75) Inventors: Anette Israelsson, Göteborg (SE); Jan Utas, Kungsbacka (SE); Agneta Pettersson, Mölndal (SE)

(73) Assignee: Astra Tech AB, Molndal (SE)

( * ) Notice: Subject to any disclaimer, the term of this patent is extended or adjusted under 35 U.S.C. 154(b) by 0 days.

(21) Appl. No.: 09/913,241

(22) PCT Filed: Feb. 14, 2000

(86) PCT No.: PCT/SE00/00289

§ 371 (c)(1),
(2), (4) Date: Dec. 11, 2001

(87) PCT Pub. No.: WO00/47494

PCT Pub. Date: Aug. 17, 2000

(30) Foreign Application Priority Data

Feb. 12, 1999 (SE) .............................. 9900465

(51) Int. Cl.[7] .............................................. B65D 81/24
(52) U.S. Cl. ...................... 206/210; 206/364; 206/438
(58) Field of Search ................................ 206/205, 207, 206/210, 363, 364, 365, 438, 440

(56) References Cited

U.S. PATENT DOCUMENTS

| | | | |
|---|---|---|---|
| 3,934,721 A | * | 1/1976 | Juster et al. ................ 206/364 |
| 3,967,728 A | | 7/1976 | Gordon et al. |
| 4,379,506 A | * | 4/1983 | Davidson ..................... 206/364 |
| 4,597,765 A | * | 7/1986 | Klatt ........................... 206/210 |
| 4,754,877 A | * | 7/1988 | Johansson et al. .......... 206/364 |
| 5,125,416 A | * | 6/1992 | Phillips ....................... 206/364 |
| 5,226,530 A | * | 7/1993 | Golden ........................ 206/210 |
| 5,738,213 A | | 4/1998 | Whiting et al. |

FOREIGN PATENT DOCUMENTS

| | | |
|---|---|---|
| EP | 0093093 | 11/1991 |
| EP | 0217771 | 12/1991 |
| GB | 1498356 | 1/1978 |
| WO | 9416747 | 8/1994 |
| WO | 9630277 | 10/1996 |
| WO | 9726937 | 7/1997 |
| WO | 9747349 | 12/1997 |
| WO | 9819729 | 5/1998 |

* cited by examiner

Primary Examiner—Luan K. Bui
(74) Attorney, Agent, or Firm—White & Case LLP

(57) ABSTRACT

A storage package (1) contains a medical device (7) having a coated surface (8) which exhibits a reduced friction when wetted with a wetting liquid and a supply of the wetting liquid (9). The package is adapted such that the coated surface of the medical device is maintained contact with the supply of wetting liquid during storage. A good shelf-life for the medical device is achieved an where the medical device is a urethral catheter the catheter is immediately "ready-for-use" after the package has been opened.

48 Claims, 2 Drawing Sheets

STORAGE PACKAGE AND A METHOD FOR PACKAGING

FIELD OF THE INVENTION

The present invention relates to a storage package which contains a medical device having a coated surface which exhibits a reduced friction when wetted and is particularly, although not exclusively, concerned with a storage package which contains a urethral catheter having an elongate shaft which is provided with a surface coating having reduced friction when wetted. The invention further relates to a method for packaging of such a medical device.

BACKGROUND OF THE INVENTION

Urethral catheters are medical devices having an elongate shaft for insertion into the urethra of a patient for inter alia drainage of the urine in the patient's bladder, use in treating cancer of the prostace or delivering a medicament. They may be for in-dwelling in the urethra for a number of days or for intermittent self-catherisation.

A fairly recent development in the field of urethral catheters has been the formation on the elongate shaft of a surface coating which exhibits a reduced friction when wetted to facilitate insertion into the urethra. The need for facilitating the insertion of the shaft into the urethra will be readily appreciated when one considers that the outer diameter of the shaft of a catheter is typically greater than the inner diameter of the urethra. In the coated catheter this is achieved by soaking the shaft in a wetting liquid such as sterile water or saline immediately prior to insertion to make the shaft surface slippery. Prior to the development of coated catheters the elongate shafts were simply formed by uncoated plastics tubing, for example of PVC, and to facilitate insertion of the shaft it was necessary to apply to the shaft a lubricant in the form of a jelly or the like which was rather cumbersome and time-consuming. As examples of friction reducing coatings suitable for application to a catheter shaft there may be mentioned the polyvinyl pyrrolidone (PVP) hydrophilic surface coatings made known in EP-B-0 093 093 and EP-B-0 217 771 (Astra AB).

It is important that the packaging used for catheters having friction-reducing surface coatings be such as to provide the catheter with a long shelf-life because the time that a urethral catheter is held in storage prior to use can be rather lengthy. To this end, the catheter packaging needs to ensure that the friction-reducing coating on the catheter is protected, for instance against the environment. The form that the package takes, however, is complicated if the catheter is to be stored after having been subjected to a sterilising process to alleviate the risk of infection of the urinary tract by the catheter as the package will need to maintain the sterile state of the catheter. Such pre-sterilisation of the catheter has the advantage that the catheter will not need to be sterilised after the catheter storage package is opened and is especially useful when the catheter is a disposable or single-use catheter. A typical pre-sterilising process for surface coated urethral catheters involves exposing the catheter to ethylene oxide gas.

Paper packaging has hitherto been proposed for storing a surface coated urethral catheter which is to be pre-sterilised by ethylene oxide gas because the gas can pass through a paper construction. Thereby, the catheter can be placed in the package and subsequently be exposed to the sterilising gas. To this end, it is conventional for the paper packaging to be formed from a paper construction in which the paper is grid-lacquered with polyethylene and welded around its edge to a laminate of, for example, polyethylene-polypropylene, polyethylene-polyetheylene terephthalate of possibly polyetheylene-nylon. A problem encountered with such paper packages, however, is that moisture can ingress into the package during storage. If moisture penetrates to the paper package, the catheter coating will become sticky leading to the coating becoming damaged, destroyed or mutilated through adherence of the coating to the paper component of the package.

WO96/30277 (Coloplast A/S) discloses a catheter storage package where the problem of adherence of coated catheters to paper packaging is solved by inserting a plastics material adjacent to the interior surface of the paper so that the catheter cannot come into direct contact with the paper. To still enable ethylene oxide gas to gain access to the catheter surface the plastics material is provided with a number of slits. The drawback of this type of catheter package, however, is that it needs a complicated manufacturing process because the dimensions of the slits in the plastics material have to be carefully regulated so that they do not permit contact of the catheter surface with the paper without in anyway hindering access of the sterilising gas.

WO97/47349 (Astra AB) proposes a solution to this drawback associated with packages of the type disclosed in WO96/30277 by placing a coated urethral catheter in an inner container formed from a material which is permeable to a sterilising agent such as ethylene oxide gas, exposing the inner container to the sterilising agent and then enclosing the inner container in an outer container which is formed from a material which prevents access of moisture to the inner container. This "double pack" arrangement keeps the coating of the catheter sterile and dry until it is required to be used thereby overcoming the problem of the catheter coating becoming sticky due to contact with moisture and then becoming damaged due to adherence with the packaging.

A drawback of the package disclosed in WO97/47349 and the other aforementioned packages is that they do not include a supply for wetting liquid for wetting of the catheter coating prior to use of the catheter. For instance, in the case of the package disclosed in WO96/30277 the catheter coating is wetted by partially opening the package and then introducing sterile water or saline solution into the enclosure containing the catheter. In the case of the package of WO97/47349, on the other hand, the catheter is removed from the package and then soaked in sterile water or saline. Further, a problem with all the above mentioned packages are that the user needs to have access to clean water.

WO97/26937 (Astra AB) discloses a package which includes a supply of sterile wetting liquid in combination with a coated catheter. In this package a coated bladder drainage catheter is positioned in a urine collection bag together with a sealed wetting liquid container, containing sterile wetting liquid. This arrangement is then exposed to ethylene oxide gas to sterilise the catheter and surfaces of the bag and container and subsequently enclosed in a moisture proof outer casing for storage. In use, the outer casing is removed and the wetting liquid container ruptured to release the sterile wetting liquid contained therein into the bag for the catheter to soak in for wetting of the surface coating. The duly wetted catheter is then projected through a removable section of the bag into the urethra with urine drained from the bladder being captured in the collection bag.

As will be appreciated by the foregoing, the development of the prior-art storage packages for a catheter having a friction-reducing surface coating has been, in the direction of keeping the coating dry during storage. The present invention is based on the insight that the real problem is not the coating coming into contact with moisture per se but more the cyclical effect of the coating coming into contact with moisture and then drying out.

WO98/19729 (Coloplast A/S) discloses a ready-to-use storage package. The storage package according to this publication is formed by wetting the hydrophilic coating of the catheter with a wetting liquid prior to its encapsulation in the storage package. The walls of the storage package are formed from a gas impermeable material which prevents drying out and keeps the hydrophilic coating wet and "ready-to-use". However, in this ready-to-use package a very limited amount of wetting liquid is supplied. When the catheter is wetted before placing it in the storage package the amount or water is naturally limited only to the amount adopted by the hydrophilic surface, and even in the embodiment where the wetting liquid is supplied after the placement of the catheter in the package, the amount of wetting liquid is limited only to the amount needed for the preparation of the hydrophilic surface of the catheter.

SUMMARY OF THE INVENTION

According to the present invention there is provided a storage package which contains a medical device having a coated surface which exhibits a reduced friction when wetted with a wetting liquid and a supply of the wetting liquid. The storage package is characterized in that, during storage, the coated surface of the medical device is constantly maintained in direct contact with said wetting liquid.

The storage package of the present invention therefore differs from that taught in WO98/19729 in that the medical device is maintained in direct contact with the wetting liquid. A problem with the catheter according to WO 98/19729 is that the possibilities for sterilisation are limited. This problem will be discussed more in detail below.

With the present invention there is no need for the coating on the medical device to be subjected to a wetting step after the package is opened since it is kept wet during storage. The package also provides the medical device with a long shelf-life, e.g. 3–5 years, due to the problem of the coating cyclically becoming wet and then drying out through moisture ingress being alleviated.

A further advantage of the package of the invention is that the medical device and the wetting liquid can be steam sterilised. Hereby, both the medical device and the wetting liquid could be sterilised at the same time, which render the sterilisation process faster and more effective. To make a steam sterilisation of the medical device possible it must be of a material having a melting temperature exceeding 100° C., and preferably exceeding 130° C. at least in the part where the surface coating (8) is provided. Such suitable materials may be polyurethanes, polyether block amides, silicon rubber, elastomeric alloys such as Santoprene® and polyolefin. alloys based on polypropylene or SEBS (Styrene Ethylene Butadiene Styrene). An example of a polyether block amide that could be used for forming the medical device is Pebax® (Elf Atochem S.A.).

The steam-sterilisation technique is Preferred, since it has the advantage over ethylene oxide gas and β- or γ-radiation sterilisation that there is no formation or absorption of harmful reaction products in the wetting liquid, in the catheter material or in the catheter surface coating.

More specifically, a problem with using ethylene oxide sterilisation is that an amount of residual ethylene oxide or degradation products are absorbed by the wetting liquid or the medical device, which could be harmful for the user of the medical device. Further, ethylene oxide could only be used for sterilising the medical device, where after the medical device and sterile wetting liquid must be aseptically packaged. However, the provision of such an aseptic environment for the packaging is both expensive and difficult to achieve in practice. Those problems with the ethylene oxide sterilisation could be overcome by using steam-sterilisation instead.

Further, a problem with β- or γ-radiation sterilisation is that harmful reaction products are likely to be produced in the medical device. The radiation also starts a degradation process in the material of the medical device, which is typically a plastic material or the like, whereby the shelf-life is shortened. Still further, the medical device has to be sterilised either before it is placed in the package together with the wetting liquid or within a short period theratfer. The pre-sterilisation of the medical device is not preferred, since it requires an aseptic packaging environment, as is discussed above. If a non-sterilised object is placed in a sterilised liquid the liquid is pre-contaminated, and the pre-contamination increases over the time. If the pre-contamination becomes too large, the sterilisation process will not be able to sufficiently sterilise the product. Further, a too large pre-contamination gives rise to large, and possibly harmful endotoxine levels. However, it may be difficult to perform the radiation sterilisation within a prescribed time period, since radiation sterilisation equipment is large and expensive, and it not realistic to have a such an equipment on each packaging facility. However, steam-sterilisation equipment are much less expensive. Hence, all the referred problems with radiation sterilisation could be overcome by using steam-sterilisation instead.

However, it should be understood that the invention is not limited to steam-sterilisation, but other sterilisation processes, such as microwave-sterilisation, with similar performance could be used as well.

In an embodiment of the invention the medical device has a shaft for insertion into a body cavity or body passageway which presents the coated surface. Examples of such medical devices are catheters such as urethral catheters for bladder drainage. The coated surface may be a surface provided with a hydrophilic coating, for example made in accordance with EP-B-0 093 093 and EP-B-0 217 771 supra and the wetting liquid may be an aqueous solution.

Where the medical device has a coated shaft for insertion into a body cavity or body passageway the wetting liquid may contain an osmolality-increasing agent such as sodium chloride and/or a pharmaceutically active substance: The wetting liquid could also contain a substance which acts to maintain the catheter and wetting liquid sterile during an extended storage period, for example an anti-bacterial agent.

In an embodiment of the invention the storage package comprises a Container within which the coated surface and the wetting liquid are contained. Further, in this embodiment, the container preferably defines a cavity which houses the coated surface and the wetting liquid is contained in the cavity in a volume sufficient for the coated surface to remain constantly wetted thereby during storage. Preferably, the cavity encloses the whole of the medical device. This facilitates the use of steam sterilisation because the wetting liquid will act to provide a uniform sterilisation temperature around the medical device.

The container may be flexible or stiff and is conveniently constructed so as to be impermeable or substantially impermeable to the wetting liquid. The container may, however, be an inner container with the package further comprising an outer container which encloses the inner container. In this case, the inner container need not be of a construction which is totally impermeable to the wetting liquid if the outer container also has good impermeability to the wetting liquid. The inner container could in this instance be made from polyurethane or polypropylene.

According to the invention there is further provided a method for sterile packaging of a medical device having a surface which exhibits a reduced friction when wetted with a wetting liquid, comprising the steps of: providing a container, placing the medical device in the container together with wetting liquid in such a way that it is maintained in contact with the wetting liquid during storage, and sterilising the medical device and the wetting liquid, and sealing the container.

According to the invention there is still further provided a ready-to-use urinary catheter assembly comprising a container, said container containing a urinary catheter having a hydrophilic surface layer which exhibits a reduced friction when wetted with a wetting liquid and a supply of the wetting liquid characterized in that, during storage, the whole of the coated surface is constantly maintained in direct contact with said wetting liquid.

These and other objects and features of the invention will become more fully apparent from the following description and appended claims.

BRIEF DESCRIPTION OF THE DRAWINGS

In the following, the invention will be explained more in detail by way of an embodiment, and with reference to the appended drawings, on which.

DESCRIPTION OF EXEMPLARY EMBODIMENT OF THE INVENTION

Figure 1:
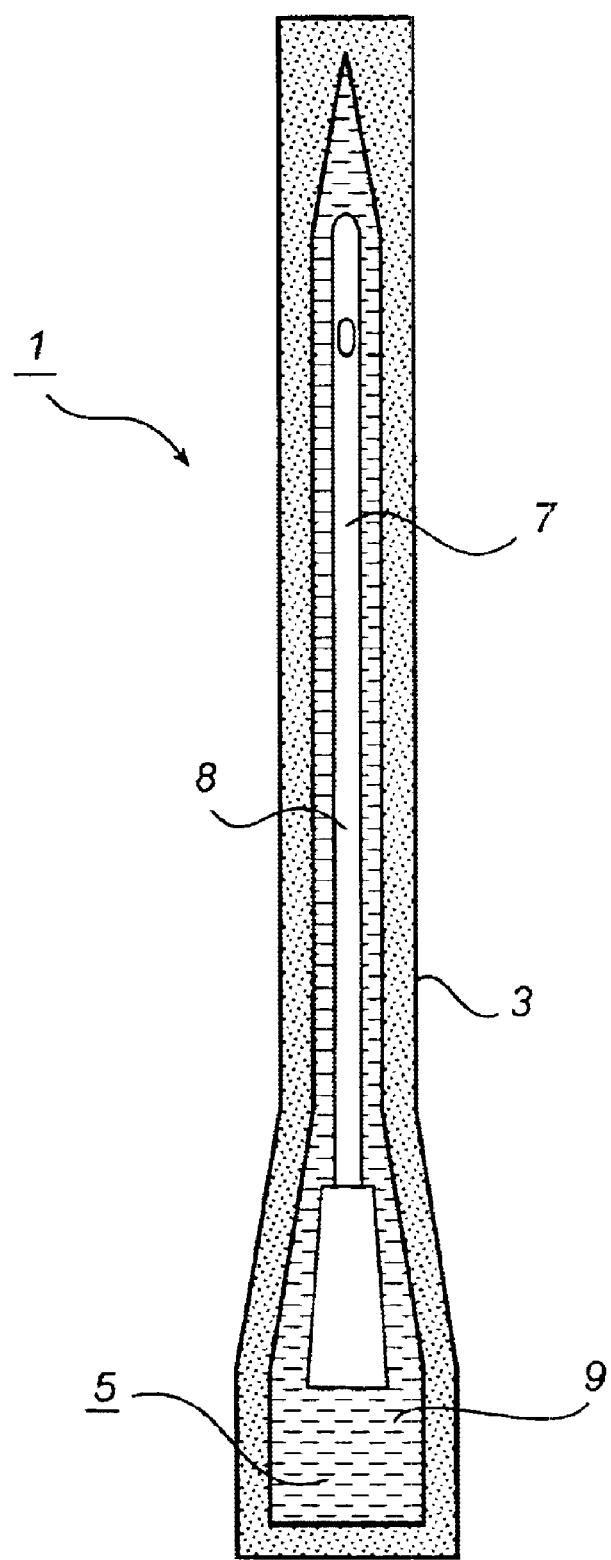
FIG. 1 shows a storage package according to a first embodiment of the invention.

By way of example, there is shown in the accompanying FIG. 1 a steam sterilised catheter storage package 1 in accordance with the present invention comprising a container 3 formed from two overlapping blanks of material heat sealed together at their periphery to from a central closed cavity 5. The cavity 5 is filled with a sterile aqueous solution 9 and further houses a urethral bladder drainage catheter 7 having a shaft 8 formed from Pebax® on which there is provided a hydrophilic coating in accordance with European patent No. 0093093 or 0217771 supra. However, other materials having a melting temperature exceeding 100° C. and preferably exceeding 130° C. could be used as well, such as polyurethanes, polyether block amides, silicon rubber, elastomeric alloys such as Santoprene® and polyolefin alloys based on polypropylene or SEBS (Styrene Ethylene Butadiene Styrene).

The blanks of material forming the container 3 are made from a construction, which is impermeable or substantially impermeable to the aqueous solution 9. Further, the blanks are preferably also of a material with a melting temperature exceeding 100° C, and preferably exceeding 130° C. As an example, the blanks may comprise a material with barrier properties, rendering it impermeable to the wetting liquid, such as aluminium oxide, polychlorotrifluoroethyelen (PCTFE), polyvinylidenechloride (PVtC), an aluminium foil or silicon oxide. Further, the blanks preferably comprise a carrier material and/or a material able to be welded, laminated with the material exhibiting the barrier properties. The skilled man in the art of packaging will know of many other materials and constructions which would work equally as well.

As will be appreciated, the package 1 results in the hydrophilic coating on the shaft 8 of the catheter 7 being maintained in a wet condition during storage. The catheter is therefore immediately ready for insertion into the urethra after the container 3 is opened. Moreover, the coating on the shaft 8 is not subjected to moisture-induced wetting and drying cycles due to the coating being stored in a wet condition. The package 1 thus ensures a long shelf-life for the catheter 7.

Figure 2:
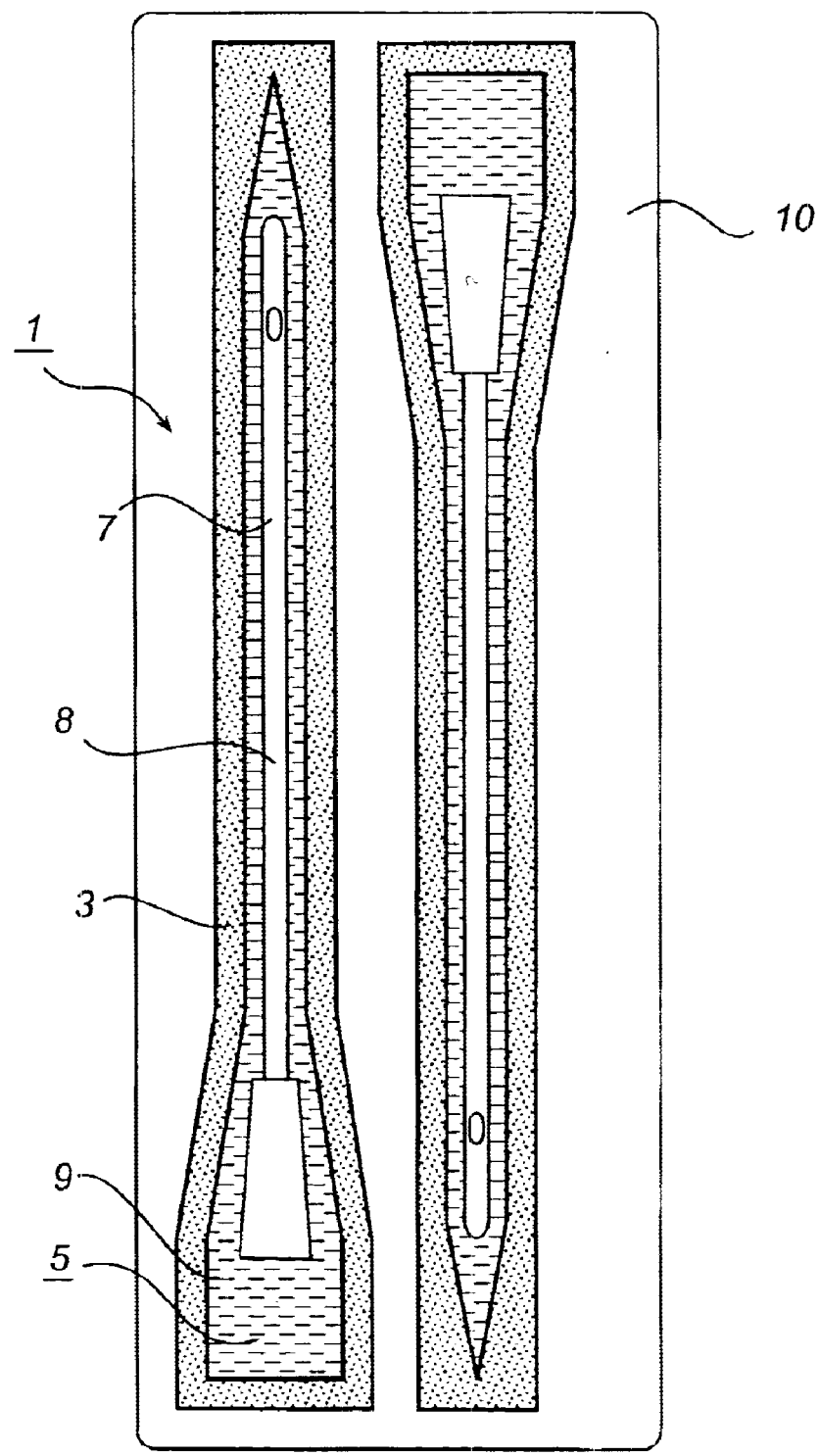
FIG. 2 shows a storage package with an additional outer container according to a second embodiment of the invention.

By reference to FIG. 2, for added security during storage the container 3 may be enclosed by an outer container 10. The container 3 could also be modified so as to act as an applicator for inserting the catheter shaft 8 into the urethra. There would thus be no risk of the catheter shaft 8 being contaminated during insertion into the urethra since the user would grip the catheter 7 through the material of the container 3. As an example, the container 3 could take the form of a urine collection bag through which the shaft 8 of the catheter 7 is projectable into the urethra of a patient with the urine drained by the catheter 7 being collected in the bag.

While the invention has been illustrated with reference to a urethral bladder drainage catheter it will be appreciated that the invention has equal application for any medical device provided with a coated surface which exhibits a reduced friction when wetted.

What is claimed is:

1. A storage package comprising a supply of a wetting liquid, a urinary catheter having a coated surface which exhibits reduced friction when wetted with the wetting liquid, and a container within which the catheter and the wetting liquid are contained, wherein the coated surface comprises a coating on a substrate comprising a polyether block amide, and wherein during storage, the coated surface of the urinary catheter is constantly maintained in direct contact with said wetting liquid.

2. The storage package as claimed in claim 1, wherein the container defines a cavity which houses the catheter and the wetting liquid is contained in the cavity in a volume sufficient for the coated surface to remain constantly wetted thereby during storage.

3. The storage package as claimed in claim 2, wherein the cavity is substantially filled with the wetting liquid.

4. The storage package as claimed in claim 2 or 3, wherein the cavity encloses the whole of the urinary catheter.

5. The storage package as claimed in claim 1, wherein the container is of a construction which is impermeable or substantially impermeable to the wetting liquid.

6. The storage package as claimed in claim 1, wherein the container is an inner container and the package further comprises an outer container which encloses the inner container.

7. A storage package, comprising a container which defines a closed cavity, a urinary catheter positioned in the closed cavity and having a coated polyether block amide substrate surface supporting a surface coating which exhibits a reduced friction when wetted with a wetting liquid, and a volume of the wetting liquid in the closed cavity sufficient for the surface coating to be maintained constantly wetted thereby during storage.

8. The storage package as claimed in claim 7, wherein during storage, substantially the whole coated substrate surface of the urinary catheter is constantly maintained in direct contact with said wetting liquid.

9. The storage package as claimed in claim 7, wherein during storage, substantially the whole of the urinary catheter is constantly maintained in direct contact with said wetting liquid.

10. The storage package as claimed in claim 7, wherein the surface coating is provided on a substrate having a melting temperature exceeding 100° C.

11. The storage package according to claim 10, wherein the urinary catheter is steam-sterilized.

12. The storage package as claimed in claim 7, wherein the container is formed of a material having a melting temperature exceeding 100° C.

13. The storage package as claimed in claim 12, wherein the container is steam-sterilized.

14. The storage package as claimed in claim 7, wherein the container is impermeable to the wetting liquid.

15. The storage package according to claim 7, wherein the wetting liquid is steam-sterilized.

16. The storage package according to claim 7, wherein the wetting liquid contains an osmolality-increasing agent and/or a pharmaceutically active substance.

17. The storage package as claimed in claim 7, wherein the surface coating is provided on a substrate having a melting temperature exceeding 130° C.

18. The storage package according to claim 7, wherein the urinary catheter is steam-sterilized.

19. The storage package as claimed in claim 7, wherein the container is formed of a material having a melting temperature exceeding 130° C.

20. The storage package according to claim 16, wherein the osmolality-increasing agent is sodium chloride.

21. A ready-to-use urinary catheter assembly comprising a container, said container containing a urinary catheter having a hydrophilic layered surface which exhibits a reduced friction when wetted with a wetting liquid, wherein the container is pre-filled with an unenclosed supply of the wetting liquid, whereby during storage, the whole of the hydrophilic layered surface is constantly maintained in direct contact with said wetting liquid.

22. A method for sterile packaging of a urinary catheter having a surface which exhibits a reduced friction when wetted with a wetting liquid, comprising the following steps:
   providing a container;
   placing the urinary catheter in the container together with the wetting liquid in such a way that the surface of the urinary catheter is maintained in contact with the wetting liquid during storage;
   sterilizing the urinary catheter and the wetting liquid; and
   sealing the container.

23. The method as claimed in claim 22, wherein the urinary catheter and the wetting liquid are sterilized at the same time.

24. The method as claimed in claim 22 or 23, wherein steam-sterilization is used for sterilizing at least one of the urinary catheter and the wetting liquid.

25. The method as claimed in claim 22 or 23, wherein microwave-sterilization is used for sterilizing at least one of the urinary catheter and the wetting liquid.

26. The method as claimed in any one of claims 22 or 23, wherein the sterilization of the wetting liquid is performed after the sealing of the container.

27. The method as claimed in any one of claims 22 or 23, wherein the sterilization of the urinary catheter is performed after the sealing of the container.

28. The method as claimed in any one of claims 22 or 23, wherein the volume of the wetting liquid placed in the container is sufficient for the surface to remain constantly wetted thereby during storage.

29. The method as claimed in any one of claims 22 or 23, wherein the step of placing wetting liquid in the container comprises placing an amount of the wetting liquid in the container such that during storage, substantially the whole surface of the urinary catheter is constantly maintained in direct contact with said wetting liquid.

30. The method as claimed in any one of claims 22 or 23, wherein the step of placing the wetting liquid in the container comprises placing an amount of wetting liquid in the container such that during storage, substantially the whole urinary catheter is constantly maintained in direct contact with said wetting liquid.

31. The method as claimed in any one of claims 22 or 23, wherein the container is an inner container, comprising the additional step of enclosing the inner container in an additional outer container.

32. The method as claimed in any one of claims 22 or 23, wherein the surface comprises a surface coating on a substrate, wherein the substrate comprises a material having a melting temperature exceeding 100° C.

33. The method as claimed in claim 32, wherein the substrate is a material selected from the group consisting of polyurethanes, polyether block amides, silicon rubber, elastomeric alloys, and polyolefin alloys based on polypropylene or SEBS (Styrene Ethylene Butadiene Styrene).

34. The method as claimed in any one of claims 22 or 23, wherein the container is formed of a material substantially impermeable to the wetting liquid.

35. The method as claimed in any one of claims 22 or 23, wherein the container is formed of a material having a melting temperature exceeding 100° C.

36. The method as claimed in any one of claims 22 or 23, comprising the further step of adding an osmolality-increasing agent and/or a pharmaceutically active substance to the wetting liquid.

37. The method as claimed in any one of claim 22 or 23, wherein the urinary catheter is immediately "ready-for-use" after the package has been opened.

38. The method as claimed in any one of claims 22 or 23, wherein the surface comprises a surface coating on a substrate, wherein the substrate comprises a material having a melting temperature exceeding 130° C.

39. The method as claimed in any one of claims 22 or 23, wherein the container is formed of a material having a melting temperature exceeding 130° C.

40. The method as claimed in claim 36, wherein the osmolality-increasing agent is sodium chloride.

41. A storage package comprising a unrinary catheter having a coated surface which exhibits a reduced friction when wetted with a wetting liquid and a supply of the wetting liquid, wherein the storage package is pre-filled with an unenclosed supply of the wetting liquid, whereby the coated surface of the a urinary catheter is constantly maintained in direct contact with the wetting liquid during storage.

42. The storage package as claimed in claim 41, wherein the storage package comprises a container within which the coated surface and the wetting liquid are contained.

43. The storage package as claimed in claim 42, wherein the container defines a cavity which houses the coated surface and the wetting liquid is contained in the cavity in a volume sufficient for the coated surface to remain constantly wetted thereby during storage.

44. The storage package as claimed in claim 43, wherein the cavity is substantially filled with the wetting liquid.

45. The storage package as claimed in claim 43, wherein the cavity encloses the whole of the urinary catheter.

46. The storage package as claimed in claim 42, wherein the container is of a construction which is impermeable or substantially impermeable to the wetting liquid.

47. The storage package as claimed in claim 42, wherein the container is an inner container and that the package further comprises an outer container which encloses the inner container.

48. The storage package as claimed in claim 41, wherein the coated surface comprises a coating on a substrate, wherein the substrate comprises a polyether block amide.

* * * * *